and Patent

United States Patent
Kim et al.

(10) Patent No.: US 7,005,282 B2
(45) Date of Patent: Feb. 28, 2006

(54) ENZYMES COATED WITH IONIC LIQUID

(75) Inventors: Mahn-Joo Kim, Pohang (KR); Jae Kwan Lee, Suwon (KR)

(73) Assignee: POSCO and POSTECH Foundation, Kyungsangbuk-do (KR)

( * ) Notice: Subject to any disclaimer, the term of this patent is extended or adjusted under 35 U.S.C. 154(b) by 0 days.

(21) Appl. No.: 10/471,190

(22) PCT Filed: Jan. 13, 2003

(86) PCT No.: PCT/KR03/00067

§ 371 (c)(1),
(2), (4) Date: Sep. 10, 2003

(87) PCT Pub. No.: WO03/057871

PCT Pub. Date: Jul. 17, 2003

(65) Prior Publication Data

US 2004/0087462 A1    May 6, 2004

(51) Int. Cl.
*C12N 9/96* (2006.01)
(52) U.S. Cl. ...................... 435/188; 435/280; 424/94.3
(58) Field of Classification Search ............... 424/94.3; 435/188, 280
See application file for complete search history.

(56) References Cited

OTHER PUBLICATIONS

Kwang-Wook Kim, Boyoung Song, Min-Young Choi, and Mahn-Joo Kim. 2001. Biocatalysis in Ionic Liquids: Markedly Enhanced Enantioselectivity of Lipase., Organic Letters, 3(10): 1507-1509.*

Wasserscheid, Peter and Keim, Wilhelm. 2000. Ionic liquids—New "solutions" for transition metal catalysis., Angew. Chem. Int. Ed., 39: 3772-3789. Pertinent p.: 3776.*

Mori, T. et al., "A Lipid-Coated Lipase as an Efficient Hydrolytic Catalyst in the Two-Phase Aqueous-Organic System", Biotechnology and Bioengineering (2001), 76(2), pp. 157-163.

Okahata, Y. et al., "Enzyme-Lipid Complex. 9. Enhancing Enantioselectivity of a Lipid-Coated Lipase via Imprinting Methods for Esterification in Organic Solvents", Tetrahedron: Asymmetry (1995), 6(6), pp. 1311-1322.

Markus Erbeldinger, Anita J. Mesiano, and Alan J. Russell, "Enzymatic Catalysis of Formation of Z-Aspartame in Ionic Liquid—An Alternative to Enzymatic Catalysis in Organic Solvents," Biotechnol. Prog., vol. 16, Dec. 31, 2000, pp. 1129-1131; and.

Kwang-Wook Kim, Boyoung Song, Min-Young Choi, and Mahn-Joo Kim, "Biocatalysis in Ionic Liquids: Markedly Enhanced Enantioselectivity of Lipase," Organic Letters, vol. 3(10), Mar. 17, 2001, pp. 1507-1509.

* cited by examiner

*Primary Examiner*—Francisco C. Prats
*Assistant Examiner*—Susan E. Fernandez
(74) *Attorney, Agent, or Firm*—Baker Botts LLP

(57) ABSTRACT

Disclosed is an ionic liquid-coated enzyme, wherein the ionic liquid is an organic salt which presents as a liquid phase at a temperature of about 150° C. or below. The ionic liquid-coated enzyme according to the present invention remarkably improves enzyme functions, such as enantioselectivity and stability, when the enzyme which may be lipase is coated with an ionic liquid. Further, even in the case of when the ionic liquid-coated enzyme is reused, the enantiomeric excess, enantioselectivity, and activity are not degenerated. The coated enzyme is usable as a catalyst for providing a chiral intermediate required in the synthesis of chiral pesticides, medicines, natural chemicals, and so on.

6 Claims, No Drawings

ENZYMES COATED WITH IONIC LIQUID

BACKGROUND OF THE INVENTION (a) Field of the Invention

The present invention relates to an enzyme coated with an ionic liquid and more particularly, to the preparation and use of an enzyme coated with an ionic liquid, which shows better enantioselectivity than its uncoated counterpart and can be repeatedly reused with no significant loss in catalytic activities.

(b) Description of the Related Art

Enzymatic kinetic resolution of racemic substrates using hydrolytic enzymes provides a useful methodology for the preparation of optically active compounds. Among the hydrolytic enzymes, lipases (lipid-hydrolyzing enzymes) are of great use since they show broad substrate specificity. Lipases are particularly useful in the resolution of racemic alcohols and their esters in organic solvents. However, they often exhibit unsatisfactory enantioselectivity, resulting in a poor resolution. Accordingly, it is highly important to develop new methods for enhancing the lipase enantioselectivity.

Various techniques have been so far developed for solving the enantioselectivity problem, A representative approach is the coating of enzyme with a lipid (Okahata, Y.; Hatano, A.; Ijiro, K. *Tetrahedron: Asymmetry* 1995, 6, 1311) or a surfactant (Huang, S. Y.; Chang, H. L; Goto, M. *Enzyme Microb. Technol.*, 1998, 22, 552). However, these methods are rather complicated to follow and cause loss in enzyme activities.

SUMMARY OF THE INVENTION

The object of the present invention is to provide a coated enzyme having better enantioselectivity and reusability compared to its uncoated native counterpart.

Another object of the present invention is to provide a method of preparing a coated enzyme having better enantioselectivity and reusability compared to its uncoated native counterpart.

Another object of the present invention is to provide a method of preparing an optical isomer using the coated enzyme.

To active these objects, the present invention provides an enzyme coated with an ionic liquid (herein, an ionic liquid is defined as an organic salt present as a liquid phase at a temperature of around 150° C. or below).

The present invention also provides a method of preparing an ionic liquid-coated enzyme comprising the steps of: dissolving the ionic liquid suitable for coating the enzyme, at a temperature of its melting point or above; mixing the dissolved ionic liquid with the enzyme; and cooling the mixture at room temperature to solidify the ionic liquid coated on the enzyme.

The present invention still further provides a method of preparing an optical isomer having a high Enantiomeric Excess comprising the steps of selectively reacting any one enantiomer of a racemic compound with an ionic liquid-coated enzyme.

DETAILED DESCRIPTION OF THE PREFERRED EMBODIMENTS

A more complete appreciation of the invention, and many of the attendant advantages thereof, will be readily apparent as the same becomes better understood by reference to the following detailed description.

The present invention describes the preparation of an ionic liquid coated enzyme (ILCE) and its use in the kinetic resolution of racemic alcohols. The term "ionic liquid" herein means an organic salt which presents as a solid phase at room temperature, while it typically presents as a liquid phase at its melting temperature of 150° C. or below. A solid ionic liquid (example: 1-alkyl-3-methylimidazolium hexafluorophosphate) as the enzyme-coating material is synthesized in two steps from 1-methylimidazole.

Many studies regarding the use of these ionic liquids as the solvents for catalysis (Wasserscheid, P.; Wilhelm, K. *Angew. Chem. Int Ed.* 2000, 39, 3772) have showed that ionic liquids have great potential as alternatives to conventional organic solvents because they are environmentally benign due to high boiling points and improve the activity and selectivity of catalysts. Studies on biocatalytic reactions in ionic liquid have also showed various advantages such that the activity and enantioselectivity of enzymes are improved, when compared to a biocatalytic reaction in a conventional organic solvent (Kim, K. W.; Song, B.; Choi, M. Y.; Kim, M. -J. *Org. Lett.* 2001, 3, 1507.; Erbeldinger, M.; Mesiano, A. J.; Russell, A. J. *Biotechnol. Prog.* 2000, 16, 1131.; Lau, R. M.; Rantwijk, F. van; Seddon, K. R.; Sheldon, R. A. *Org. Lett.* 2000, 2, 4189.).

The ionic liquid for coating an enzyme presents as a solid phase at room temperature and turns to a liquid phase upon heating to a temperature of its melting point or above. The ionic liquid, thus, presents as a liquid phase at a temperature of 150° C. or below, and preferably at a temperature of between 120° C. and 150° C.

An organic cation of an ionic liquid may include a cation of a heterocyclic compound, and an organic or inorganic anion forming an ionic bond with the cation thereof.

The heterocyclic compound is composed of at least one heteroatom selected from the group consisting of N, O, S, or a combination thereof, and the number of heteroatoms is preferably 1 to 4 and more preferably 1 to 2. The cation of the heterocyclic compound is a cation of a compound selected from the group consisting of imidazolium, pyridinium, pyridazinium, pyrimidinium, pyrazinium, pyrazolium, thiazolium, oxazolium, triazolium, and a substituted compound thereof.

The organic or inorganic anion may be any one of bis(perfluoroethyl sulfonyl)imide $(N(C_2F_5SO_2)_2^-)$, bis(trifluoromethyl sulfonyl)imide $(N(CF_3SO_2)_2^-)$, tris(trifluoromiethyl sulfonyl)methide $(C(CF_3SO_2)_2^-$, trifluoromethane sulfonimide, trifluoromethyl sulfonimide, trifluoromethyl sulfonate, $AsF_6^-$, $ClO_4^-$, $PF_6^-$, and $BF_4^-$.

The ionic liquid according to present invention is preferably represented by the following Formula 1:

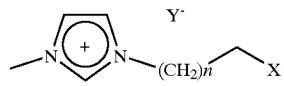

Formula 1 wherein

X is selected from the group consisting of phenyl, substituted phenyl, methacryloyl ester, $OCOCH_3$, $CO_2CH_3$, and CN;

Y is $BF_4$ or $PF_6$; and n is an integer of 2 to 5.

The substituted phenyl group is a phenyl group having at least one substituent selected from the group consisting of a $C_{1-3}$ alkyl, a $C_{1-3}$ alkoxy, an ester, an amide, hydroxy, cyano, a halogen, and nitro.

A method of preparing an ionic liquid-coated enzyme (ILCE) according to the present invention comprises: melting the ionic liquid suitable for coating the enzyme at a temperature of its melting point or above; mixing the melted ionic liquid with the enzyme; and cooling the mixture to solidify the ionic liquid coated on the enzyme. Coating the enzyme according to the present invention is simply achieved by mixing it in the molten ionic liquid and cooling the mixture.

The coating of enzyme is initiated by heating the solid ionic liquid up to over its melting point to get its liquid phase, followed by the addition of enzyme powders. The resulting heterogeneous mixture is then allowed to cool down to get a solid solution, Finally, the solid solution is made small particles with a spatula. The small particles as an ILCE are used as the catalysts for the resolution of racemic alcohols. The ILCE exhibits 1.5–2 times better enantioselectivity compared to its uncoated native enzyme.

The ionic liquid suitable for coating the enzyme may be obtained commercially or synthesized according to the conventional method known to anyone having ordinary skill in the art. For example, 1-(3-phenylpropyl)-3methylimidazolium hexafluorophosphate represented by Formula 1 is prepared from the reaction of c with 1-chloro-3-phenylpropane to obtain 1-(3-phenylpropyl)-3-methylimidazolium chloride, and then with $HPF_6$ to exchange anions.

The amount of ionic liquid is varied depending upon the type of enzyme used, but it is preferably between 5 and 20 g per 1 g of enzyme. When the amount of ionic liquid is less than 5 g, the coating effect is insufficient. While when the amount is more than 20 g, it is not preferably since the activity per unit weight of coated enzyme is reduced.

The enzyme to be coated with the ionic liquid may include, but is not limited to, lipase, which is conveniently used in preparation of an optically active compound. Representative examples of the lipase may include *Pseudomonas cepacia* lipase (LPS), *Candida antarctica* lipase (CAL), *Candida rugosa* lipase (CRL), *Aspergillus niger* lipase (ANL), *Candida cylindracea* lipase (CCL), *Mucor miehei* lipase, *Pseudomonas fluorecens* lipase (LAK, *Rhizopus arrhizus* lipase, *Rhizopus niveus* lipase, Hog pancreas lipase, *Candida lipolytfca* lipase, *Mucor javanicus* lipase, *Penicillium roqueforti* lipase, and *Rhizomucor miehei* lipase.

Using the ionic liquid-coated enzyme as a catalyst, an optical isomer having a high enantiomeric excess (optical purity) is prepared by the enantioselective acylation of one enantiomer of a racemic compound. For example, using the ionic liquid-coated lipase, an enantiomer of racemic alcohol is selectively acylated (transesterfication) to obtain chiral esters having good enantiomeric excess.

In an optical resolution process of racemic secondary alcohols using a coated lipase, the secondary alcohol may include, but is not limited to, alcohols represented by the following Formulas 2a, 2b, 2c, and 2d:

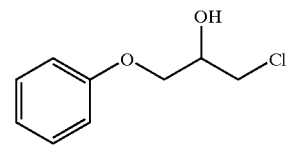

2a

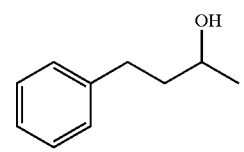

2b

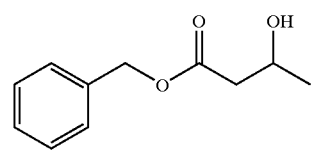

2c

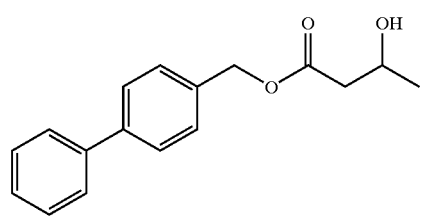

2d

The reaction solvent to be used in the reaction of an ionic liquid-coated enzyme with a racemic compound is preferably, but is not limited to, toluene, ether or hexane which does not dissolve the ionic liquid, since the yield and enantioselectivity of enzyme-catalyzed reaction is generally affected by solvent. The amount of reacting solvent is one rendering the reactant to be at a concentration of between 0.2 and 0.4 M.

Hereinafter, the present invention will be explained in detail with reference to examples and comparative examples. These examples, however, should not in any sense be interpreted as limiting the scope of the present invention.

EXAMPLE 1

Preparation of 1-(3-phenylpropyl)-3-methylimidazolium chloride 0.15 mole of 1-methylimidazole and 0.125 mole of 1-chloro-3-phenylpropane were introduced into a 100 mL round bottom flask and stirred at 70° C. for one day to obtain 1-(3-phenylpropyl)-3-methylimidazolium chloride (yield 99%).

$^1$H-NMR (CD$_3$CN, δ, 300 MHz) 2.18 (m, 2H, CH$_2$), 2.64 (t, 2H, J=7.4 Hz, CH$_2$), 3.90 (s, 1H, NCH$_3$), 4.27 (t, 2H, J=7.1 Hz, CH$_2$), 7.18–7.30 (m, 5H, C$_6$H$_5$), 7.56 (s, 1H, CH), 7.63 (s, 1H, CH), 9.94 (s, 1H, CH).

Preparation of 1-(3-Phenylpropyl)-3-methylimidazolium hexafluorophosphate 1.2 equivalents of HPF$_6$ were slowly added to 1-(3-phenylpropyl)-3-methylimidazolium chloride under ice cooling. After stirring for 30 minutes, the mixture was extracted with methylene chloride (MC) three times. The extract was dried over anhydrous sodium sulfate and concentrated to obtain 1-(3-phenylpropyl)3-methylimidazolium hexafluorophosphate (mp 52~53° C., yield 78%).

$^1$H-NMR (CD$_3$CN, δ, 300 MHz) 2.14 (m, 2H, CH$_2$), 2.65 (t, 2H, J=7.4 Hz, CH$_2$), 3.80 (s, 1H, NCH$_3$), 4.14 (t, 2H, J=7.2 Hz, CH$_2$), 7.19–7.35 (m, 7H), δ8.34 (s, 1H, CH).

EXAMPLE 2

Coating on Lipase with 1-methyl-3-(3-phenylpropyl) imidazolium Hexafluorophosphate To the molten 1 g of 1-methyl-3-(3-phenylpropyl)imidazolium hexafluorophosphate at a temperature of its melting point or above, 100 mg of lipase (LPS, lipase from *Pseudomonas cepacia*) was added. After stirring for 10 minutes, the resulting mixture was cooled to room temperature to obtain 1.1 g of coated lipase.

EXAMPLE 3

Optical Resolution of Racemic Alcohols with the Coated Lipase (LPS)

0.1 mmol of racemic alcohols represented by the following Formulas 2a to 2d, 160–400 mg of 1-methyl-3-(3-phenylpropyl)imidazolium hexafluorophosphate-coated lipase (LPS), and 0.3 mmol of vinyl acetate 0.3 mmol were mixed in 0.5 mL of toluene and the mixture was stirred at room temperature. Generally, an ionic liquid-coated enzyme is added in an amount of 5.5 to 22 times more than that of a natural enzyme in order to exert the same effect thereof.

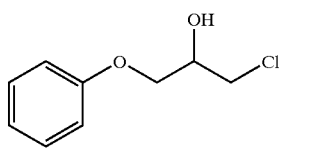

2a

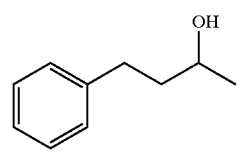

2b

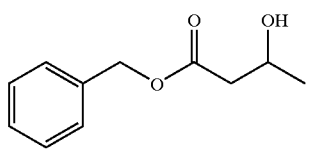

2c

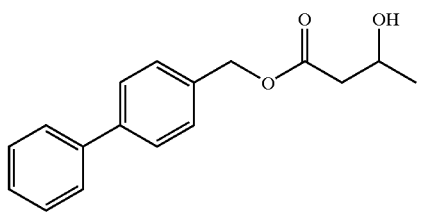

2d

The reaction was terminated when thin layer chromatography confirmed that the acylation had proceeded to around 50%. Lipase (LPS) was filtered from the reaction mixture and the solvent was evaporated. Then, the enantiomeric excesses of chiral acetate and non-acylated alcohol were measured by high performance liquid chromatography equipped with chiral column.

COMPARATIVE EXAMPLE 1

Optical Resolution of Racemic Alcohols by Natural Lipase (LPS)

The same method as in Example 3 was performed, except that 16–36 mg of natural lipase was used instead of the coated lipase (LPS).

The optical purities of chiral ester and remained racemic alcohols prepared according to Example 3 and Comparative Example 1 are shown in Table 1.

TABLE 1

| | Racemic alcohol | Enantiomeric Excess of alcohol (%) | Enantiomeric Excess of chiral ester (%) | Enantioselectivity |
|---|---|---|---|---|
| Example 3 | 2a | 37.0 | 99.5 | 574 |
| | 2b | 29.5 | 99.5 | 532 |
| | 2c | 30 | 98.3 | 156 |
| | 2d | 27.5 | 98.9 | 237 |
| Comp. Example 1 | 2a | 56.3 | 98.8 | 293 |
| | 2b | 54.5 | 98.7 | 265 |
| | 2c | 45.9 | 97.1 | 107 |
| | 2d | 57.5 | 98.3 | 161 | note)
Enantiomeric Excess (ee) = (R − S)/(R + S)

As shown in Table 1, enantioselectivity of ionic liquid-coated lipase according to Example 3 is better than or equivalent to that of the natural enzyme according to Comparative Example 1.

EXAMPLE 4

Activity of the Reused Natural LPS or the Reused Coated LPS

The coated LPS and natural LPS were reused 4 times for the resolution of racemic alcohol having Formula 2b and their activities after each reuse were measured. The results are shown in Table 2.

TABLE 2

| | Number of reuses | Converting rate of racemic alcohol at 1 day after reaction (%) | Enantiomeric excess of chiral ester (%) | Enantioselectivity |
|---|---|---|---|---|
| Example 3 | 1$^{st}$ | 37.5 | 99.3 | 524 |
| | 2$^{nd}$ | 32.9 | 99.3 | 462 |
| | 3$^{rd}$ | 34.4 | 99.5 or more | 673 or more |
| | 4$^{th}$ | 33.0 | 99.5 or more | 651 or more |
| Comp. Example 1 | 1$^{st}$ | 27.2 | 98.3 | 167 |
| | 2$^{nd}$ | 25.0 | 98.6 | 182 |
| | 3$^{rd}$ | 16.4 | 98.9 | 219 |
| | 4$^{th}$ | 9.1 | 99.2 | 275 | note)
Enantiomeric Excess (ee) = (R − S)/(R + S)

As shown in Table 2, the activity was dramatically degenerated when the natural LPS (Comparative Example 1) was reused, while the activity and enantioselectivity were not substantially reduced when the ionic liquid-coated LPS (Example 3) was reused even after four times.

The ionic liquid-coated enzyme according to the present invention remarkably improves enzyme functions, such as enantioselectivity and stability, when the lipase is coated with the ionic liquid. Further, even the case in which the ionic liquid-coated enzyme is reused, the enantiomeric excess, enantioselectivity, and activity are not substantially degenerated. The coated enzyme is usable for a catalyst for providing a chiral intermediate required in the synthesis of chiral pesticides, medicines, natural chemicals, and so on.

While the present invention has been described in detail with reference to the preferred embodiments, those skilled in the art will appreciate that various modifications and substitutions can be made thereto without departing from the spirit and scope of the present invention as set forth in the appended claims.

What is claimed is:

1. An enzyme coated with an ionic liquid, wherein the ionic liquid is an organic salt which is a liquid phase at a temperature of about 150° C. or below, wherein the ionic liquid comprises an organic cation of a heterocyclic compound and an organic or inorganic anion, the organic cation of the heterocyclic compound being selected from the group consisting of imidazolium, pyridinium, pyridazinium, pyrimidinium, pyrazinium, pyrazolium, thiazolium, oxazolium, and triazolium, or a cation of a substituted compound thereof, the organic or inorganic anion being selected from the group consisting of bis(perfluoroethyl sulfonyP)imide $(N(C_2F_5SO_2)_2^-)$, bis(trifluoromethyl sulfonyl)imide $(N(CF_3SO_2)_2^-)$, tris(trifluoromethyl sulfonyl methide $(C(CF_3SO_2)_2^-)$, trifluoromethane sulfone imide, trifluoromethyl sulfone imide, trifluoromethyl sulfonate, $AsF_6^-$, $ClO_4^-$, $PF_6^-$, $BF_4^-$, the enzyme being a lipase.

2. The ionic liquid-coated enzyme according to claim 1, wherein the ionic liquid is represented by the following Formula 1:

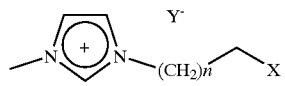

Formula 1 wherein

X is selected from the group consisting of phenyl, substituted phenyl, methacryloyl ester, $OCOCH_3$, $CO_2CH_3$, and CN;

Y is $BF_4$ or $PF_6$; and n is an integer of 2 to 5.

3. The ionic liquid-coated enzyme according to claim 1, wherein the lipase is selected from the group consisting of Pseudomonas cepacia lipase (LPS), Candida antarctica lipase (CAL), Candida rugosa lipase (CRL), Aspergillus niger lipase (ANL), Candida cylindracea lipase (CCL), Mucor miehei lipase, Pseudomonas fluorecens lipase (LAK), Rhizopus arrhizus lipase, Rhizopus niveus lipase, Hog pancreas lipase, Candida lipolytica lipase, Mucor javanicus lipase, Penicillium roqueforti lipase, and Rhizomucor miehei lipase.

4. A method of preparing an ionic liquid-coated enzyme comprising the steps of:

melting an ionic liquid suitable for coating the enzyme, at a temperature of its melting point or above, wherein the ionic liquid is an organic salt which is a liquid phase at a temperature of about 150° C. or below;

mixing the melted ionic liquid with the enzyme; and cooling the mixture to solidify the ionic liquid coated on the enzyme, wherein the ionic liquid comprises an organic cation of a heterocyclic compound and an organic or inorganic anion, the organic cation of the heterocyclic compound being selected from the group consisting of imidazolium, pyridinium, pyridazinium, pyrimidinium, pyrazinium, pyrazolium, thiazolium, oxazolium, and triazolium, or a cation of a substituted compound thereof, the organic or inorganic anion being selected from the group consisting of bis(perfluoroethyl sulfonyl)imide $(N(C_2F_5SO_2)_2^-)$, bis(trifluoromethyl sulfonyl)imide $(N(CF_3SO_2)_2^-)$, tris(trifluoromethyl sulfonyl methide $(C(CF_3SO_2)_2^-)$, trifluoromethane sulfone imide, trifluoromethyl sulfone imide, trifluoromethyl sulfonate, $AsF_6^-$, $ClO_4^-$, $PF_6^-$, and $BF_4^-$, the enzyme being a lipase.

5. The method according to claim 4, wherein the ionic liquid is represented by the following Formula 1:

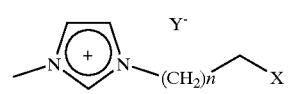

Formula 1 wherein

X is selected from the group consisting of phenyl, substituted phenyl, methacryloyl ester, $OCOCH_3$, $CO_2CH_3$, and CN;

Y is $BF_4$ or $PF_6$; and n is an integer of 2 to 5.

6. A method of preparing an optical isomer comprising the steps of selectively reacting any one enantiomer of a racemic compound with the ionic liquid-coated enzyme according to claim 1.

* * * * *